United States Patent [19]

McFee

[11] 4,052,267

[45] Oct. 4, 1977

[54] WATER DISTILLER

[76] Inventor: Richard McFee, 852 Ostrom Ave., Syracuse, N.Y. 13210

[21] Appl. No.: 593,379

[22] Filed: July 7, 1975

[51] Int. Cl.² .............. B01D 3/00; B01D 5/00
[52] U.S. Cl. ............... 202/185 B; 202/190; 202/197; 202/206; 203/2; 203/10; 203/40; 202/83
[58] Field of Search ............. 202/185 B, 185 R, 167, 202/185 C, 201, 187, 189, 181, 206, 83, 234, 235, 190–196, 197, 160, 264; 203/49, 10, 100, 20, 2, 40; 122/13 A

[56] References Cited
U.S. PATENT DOCUMENTS

| 587,506 | 8/1897 | Pierce et al. | 202/189 |
| 1,043,305 | 11/1912 | Duensing | 202/189 |
| 3,312,600 | 4/1967 | Morton | 203/10 |
| 3,350,279 | 10/1967 | Tolchin | 159/DIG. 1 |
| 3,825,491 | 7/1974 | Sanchez | 202/189 |
| 3,935,077 | 1/1976 | Dennison | 202/83 |

FOREIGN PATENT DOCUMENTS

| 25,425 | 1/1956 | Germany | 202/185 B |
| 921,492 | 3/1963 | United Kingdom | 202/185 B |

Primary Examiner—Wilbur L. Bascomb, Jr.
Attorney, Agent, or Firm—Kenyon & Kenyon, Reilly, Carr & Chapin

[57] ABSTRACT

The portable water distiller is constructed to distill water placed within a housing and to dispense it directly into a separate storage vessel or to a distilled water space in the housing. In the latter case, the distillers are provided with a flexible impermeable partition which may be in the form of a bag and which divides the interior of the housing into a raw water space and a distilled water space. A boiler is disposed within the raw water space in order to vaporize the water and a compact radiator and fan assembly is mounted on top of the housing in order to condense the vapor into distilled water for delivery to the distilled water space within the housing. A heater-thermostat shut-off means is also provided for turning off the heater when the supply of water is too low.

8 Claims, 10 Drawing Figures

WATER DISTILLER

This invention relates to a water distiller. More particularly, this invention relates to a portable water distiller.

As is known, in many communities, water used for drinking purposes has an unpleasant taste due to chlorine or minerals or suspended vegetable matter. Such water may also contain chemicals, bacteria or viruses believed to endanger health. Because distilled water has an agreeable taste and is free of dangerous substances, many householders prefer distilled water to tap or well water. However, distilled water which is sold through retail outlets is generally expensive.

It is also known that various types of devices are available to use in the home for distilling water. Unlike distillers used for scientific purposes, these home devices are not usually connected permanently to the water supply nor is tap water used for cooling steam. Rather, a pot is usually filled with water, the water turned to steam by a heater, the steam condensed by some form of air cooling, usually aided by a fan, and the distilled water is then dripped into a storage vessel. An arrangement is also usually provided for turning off the heater when the pot is almost empty. After the brine remaining in the pot has been poured off, the cycle may be repeated.

One very desirable quality of home distillers is compactness. The reason for this is that counterspace in most kitchens, particularly those in apartments, is limited. Cost is also related to size. A good measure of the compactness of a pot-type distiller is the ratio of the volume of the distiller and the storage vessel to the volume of the water distilled per cycle. Generally most distillers now available for home use are not very compact since they have ratios of the order of 7 to 10.

Another desirable quality for distillers is economical operation. An ideal (simple) distiller would make one gallon of water for every 2.6 kilowatt hours of electric power. However, the equipment now in use requires as much as 4½ kilowatt hours per gallon. In addition, another desirable quality for a distiller is low cost. The presently available distillers, however, are generally expensive and fall in the range of about $150 to $400 per unit. Such a price usually places the hygenic benefits of distilled water out of the reach of all but a few households.

Accordingly, it is an object of the invention to provide a compact water distiller.

It is another object of the invention to provide a water distiller which consumes relatively little power for each gallon of water distilled.

It is another object of the invention to provide a water distiller of relatively inexpensive construction.

It is another object of the invention to provide a water distiller which can be easily handled in a compact area.

Briefly, the invention provides a water distiller comprising a housing, a heater and a cap. The housing is sized to define a raw water storage space and has a suitable inlet for the introduction of raw water as well as a suitable outlet for removing brine or unused water. The heater is disposed in the housing for vaporizing the water in the raw water storage space. The cap which is removably mounted on the housing has a radiator therein as well as a fan. The radiator is connected in communication with the raw storage space in order to receive a flow of vapor therefrom while the fan serves to blow air over the radiator to cool the radiatior and thus condense the vapor therein to water. The cap also has an outlet connected to the radiator for dispensing the distilled water therefrom.

The distiller may also be constructed without a fan-radiator assembly. In this case, the distiller is made with a housing, a member which is removably mounted on the housing at the upper end and a boiler cap assembly mounted on this latter member. The member is of annular shape, such as a collar, to fit around the top of the housing and includes a tubular wall which depends into the housing in spaced relation in order to define a first space therebetween. The annular member also mounts a flexible impermeable bag which depends into the housing within the tubular wall. The bag serves to define a second space between the bag and wall as well as a third space in the bag. A spout is also formed on the annular member to communicate with the space between the tubular wall and the bag. The boiler cap assembly includes a boiler which depends into the bag to define a boiler space and includes a port which communicates this space with the space within the bag. The assembly also has a heater within the boiler to vaporize the water within the boiler space as well as a means which communicates the boiler space with the space between the tubular wall and housing in order to deliver the vapor thereinto for condensing purposes.

The cap which includes the fan and radiator is made as a compact unit and is made to be easily removable from the top of the housing of the distiller. Such a cap is of lightweight construction, for example the total weight of the fan-radiator cap is about two pounds. In this way, the cap is light enough to be easily handled and manipulated.

The heater is disposed inside the distiller within a confined area. This confined area may be defined by a boiler in the form of a tube which encircles the heater or in the form of a bubble catcher means which serves to guide the bubbles of vapor from the heater upwardly through the water in the raw water space to the radiator. The bubble catcher means is generally in the form of a tube open at the bottom end. Both bubble catcher and boiler may be thermally insulated and fastened within the housing in a fixed position. They may also be detachably mounted to be readily removed for cleaning out of scale without danger of wetting the fan-radiator cap which has an electric motor which should remain dry.

In the embodiments where a flexible and water impermeable partition is used, the partition is generally made of a limber fabric coated with thin layer of plastic. The simple partition is a bag. The raw water space may be the inside of the bag. In this case, when in use, raw water is poured into the bag to fill the bag and, in turn to cause the bag to fill the housing. During operation of the distiller, distilled water produced drips back via the heater and radiator into the housing on the outside of the bag. The bag then slowly collapses so that, eventually, the housing is filled almost completely with distilled water and the bag is snug up against the boiler located within the bag. This feature saves space since the need for a separate storage vessel is eliminated.

The heater-thermostat shut-off means which is used to turn-off the heater when the supply of raw water is too low may be of any suitable construction. This means generally includes a small auxiliary heater and an adjacent thermostatic switch. So long as heat is conducted away from the auxiliary heater by the water in the distiller, the temperature of the thermostat stays low enough so that the switch remains closed and power is supplied to the heater heating the water. However, when the water level falls below the auxiliary heater, the temperature of this heater rises and, therefore, the temperature of the thermostat. This, in turn, causes the thermostat to actuate a switch to shut off the power flow to the main heater. A small light may be connected in parallel with the thermostat to provide a physical indication that distillation is complete. Such heaters with built in thermostats are widely used for controlling the temperature of water in part because of their ability to shut themselves off when the water level gets too low.

These and other objects and advantages of the invention will become more apparent from the following detailed description and appended claims taken in conjunction with the accompanying drawings in which:

Figures 1, 2, 4, 5:
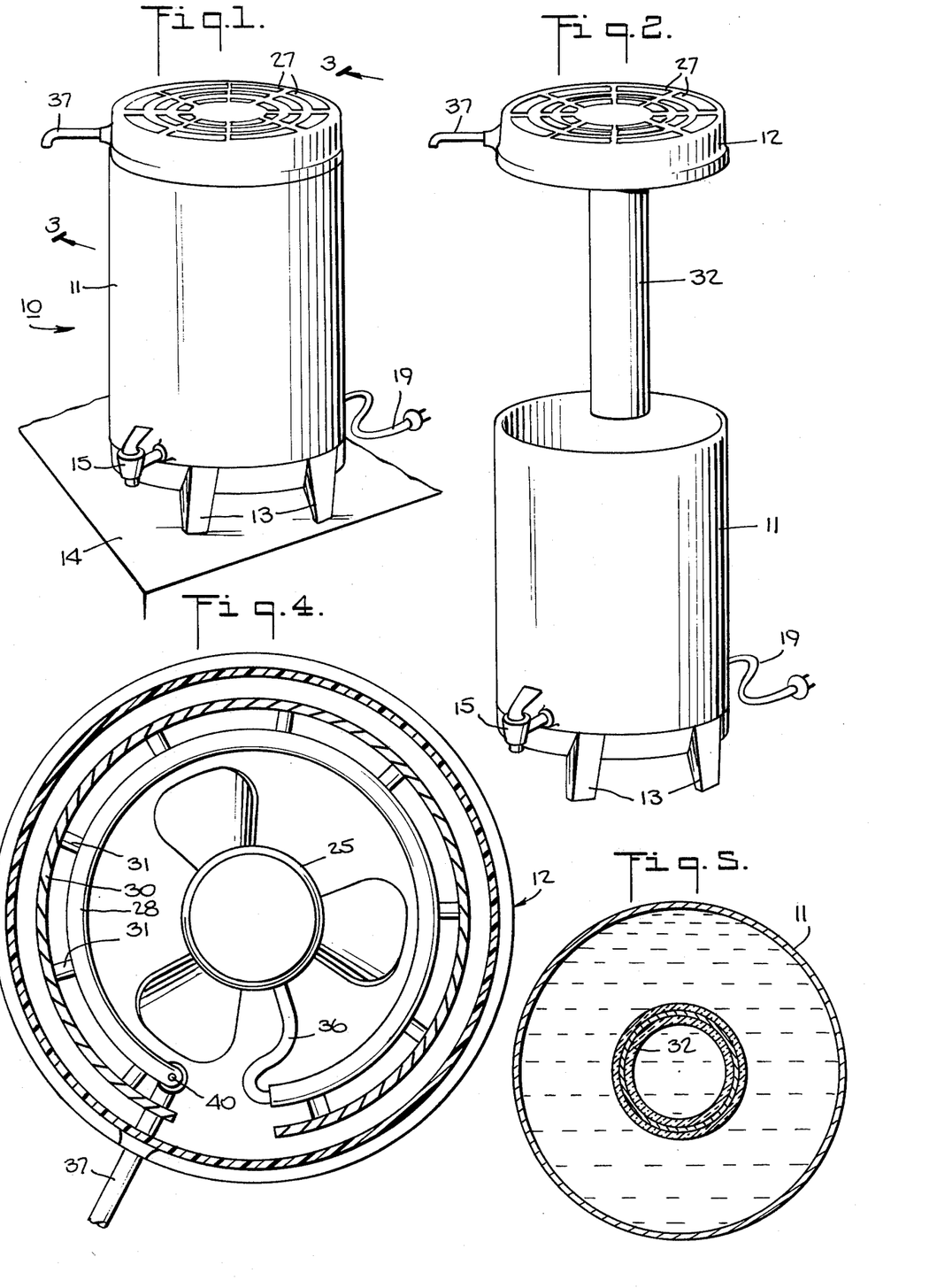
FIG. 1 illustrates a perspective view of a portable water distiller according to the invention.
FIG. 2 illustrates an exploded view of the water distiller of FIG. 1.
FIG. 4 illustrates a view taken on line IV—IV of FIG. 3.
FIG. 5 illustrates a view taken on line V—V of FIG. 3.
Figure 3:
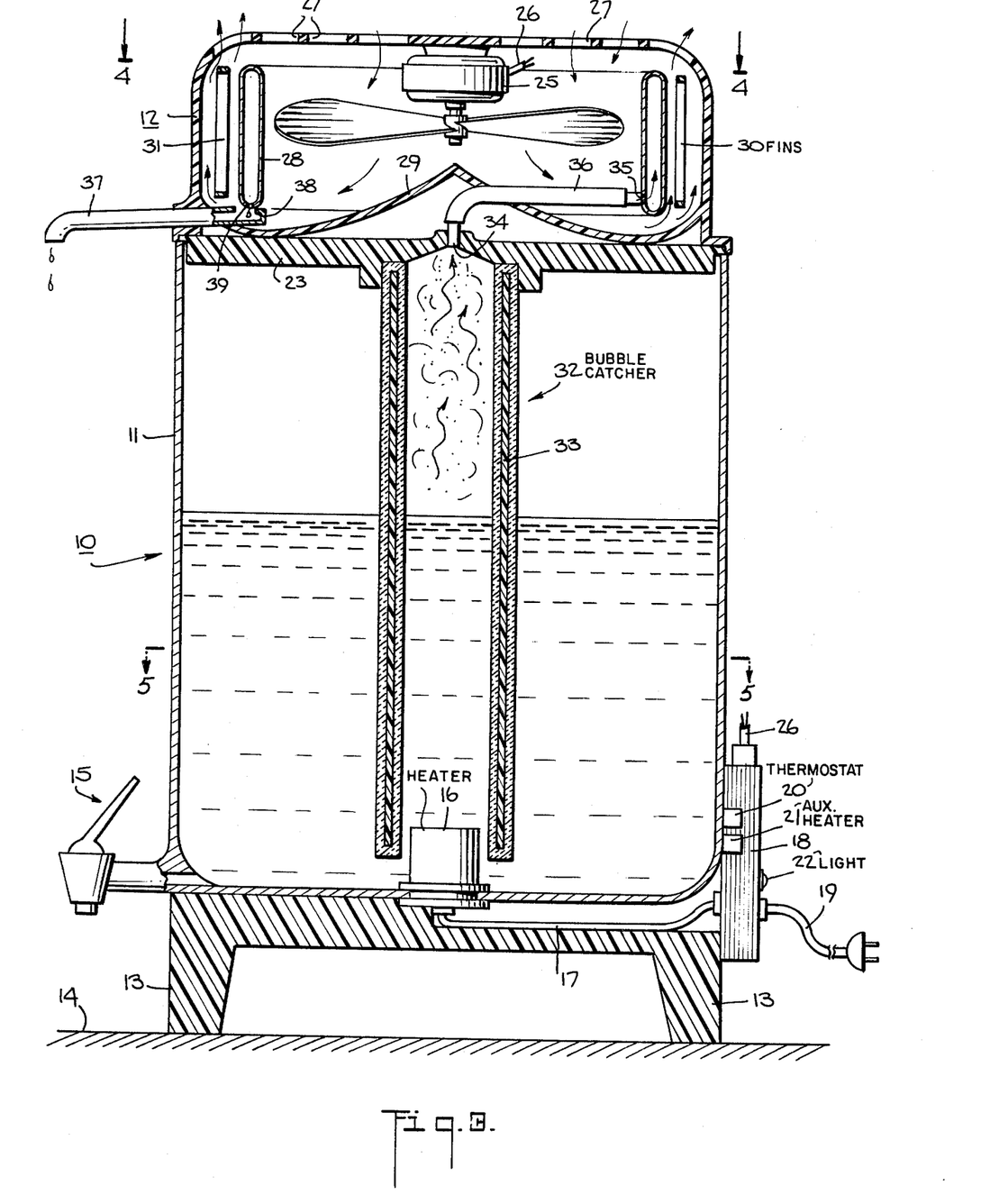
FIG. 3 illustrates a view taken on line III—III of FIG. 1.

Referring to FIG. 1, the water distiller 10 is constructed of a housing 11 and a cap 12 which is removably mounted on the housing 11. The housing 11 is of cylindrical hollow construction and is provided with suitable support legs 13 at the base to support the distiller 10, for example on a countertop 14. The housing 11 has an open top as indicated in FIG. 3. A spigot 15 is mounted at the lower end of the housing 11 to permit emptying of the contents of the housing 11. This spigot is constructed in any suitable fashion for this purpose.

Referring to FIG. 3, an electric heater 16 is disposed at the bottom of the housing 11 and is electrically connected by suitable leads 17 to terminal block 18 which, in turn, has an electric cord 19 which may be plugged into any suitable power source outlet. In addition, a thermostat-heater shut-off means is mounted on the exterior of the housing 11. This means 21 includes a thermostat 20 which is mounted to react to the heat generated by an auxiliary heater 21 so as to shut-off the main heater 16 in response to the auxiliary heater 21 generating a predetermined level of heat. In addition, an indicator light 22 is connected in parallel with the thermostat 20 to the power source so as to provide a visible indication of the shut-off condition. The auxiliary heater 21 is generally cooled by the contents of the housing 11 if the water level within the housing 11 is above the auxiliary heater 21. Thus, the heat generated by the auxiliary heater 21 is conducted away so that the temperature of thermostat 20 remains low. However, should the water level in the housing 11 drop below the level of the auxiliary heater 21, the heater 21 will be insufficiently cooled. Thus the thermostat 21 would respond to deactivate the main heater 16.

Referring to FIGS. 2 and 3, the cap 12 is made as a unit and includes a base 23 which functions as a cover to sit on top of the housing 11. The cap 12 also includes an electric fan 25 which is mounted on the interior and which has a motor connected electrically to the power block 18 by suitable lines 26. The upper end of the cap 12 is in the form of a grille provided with openings or perforations 27 to permit the inflow and outflow of air to the fan 25. In addition, the cap 12 includes a radiator 28 which is formed of one or more closed tubes which encircle the fan 25. As shown in FIG. 4, the radiator 28 is formed of a single flat closed tube which is of almost circular shape. The tube 28 and fan 25 are concentric to each other and a deflector 29 is mounted below the fan 25 within the cap 12 so as to deflect a flow of air from the fan 25 downwardly around the base of the radiator 28 and upwardly along the outside surfaces of the radiator 28. The flow of cooling air along the surfaces of the radiator 28 serves to cool the interior of the radiator 28. In addition, suitable fins are mounted in the cap 12 for dissipating heat generated within the radiator 28. For example, a fin 30 about 2¼ inches high and 5½ inches in diameter is mounted on the radiator 28 using 10 or so pieces 31 of copper bar which act as spacers and heat conductors. This fin 30 increases the surface area and hence the cooling power of the radiator 28. Alternatively, a standard fin arrangement can be used in which a multiplicity of fins are attached to the outer surface of the radiator 28. The fin may also be replaced by a second tube of slightly larger diameter through which half of the steam is passed.

Referring to FIG. 3, the cap also has a bubble catcher means 32 mounted therein. As shown, this means is in the form of a thermaly insulated tube 33 which is mounted within a suitable port 34 in the cover 23, as by threading or a press fit, coaxially of the housing. This tube 33 depends into the housing 11 about the main heater 16 almost to the bottom of the housing 11 leaving only a small gap between the tube 33 and the bottom for water to enter.

A port 34 is formed in the cover to communicate with the interior of the tube 33 and a similar port 35 is formed in one end of the radiator 28. A conduit 36 connects the two ports 34, 35 together so as to communicate the interior of the tube 33 with the interior of the radiator 28.

As shown in FIG. 3, an outlet pipe 37 is disposed in the cap 12 with an inlet opening 38 below an outlet port 39 in the end of the radiator 28.

In operation, water is initially placed in the housing 11 and thereafter the cap 12 is put in place. Next, with the distiller 10 plugged in for example via a suitable switch (not shown) the main heater 16 vaporizes the water within the immediate area and bubbles or vapor are formed which rise upwardly through in the bubble catcher tube 33. The resultant vapor or steam is then passed through the conduit 36 into the initial end of the radiator 28. The steam then fills the radiator 28 and during this time, the fan 25 is turned on so that a flow of air is passed about the radiator 28. This flow of air serves to cool the interior of the radiator 28 so that the steam condenses on the interior walls of the radiator 28. The condensed steam in the form of distilled water then flows along the bottom of the radiator 28 until reaching the outlet 39 and drips into the outlet pipe 37. The water then flows out of the pipe 37 into a suitable storage vessel (not shown).

Referring to FIG. 3, the inlet port 35 to the radiator 28 is disposed at a higher plane than the floor of the radiator 28 so that water will not backflow into the housing 11.

Referring to FIG. 4, the radiator 28 is provided with a pinhole 40 or the like coaxially above the outlet for the distilled water. This pinhole 40 serves to increase the efficiency of the distiller 10.

Should the water level in the housing 11 fall below the level of the auxiliary heater 21 (FIG. 3) the thermostat 20 will be actuated as described above. This, in turn, will deactivate the main heater 16 as well as the fan 25. Alternatively, the fan 25 may be connected via a delay switch so that the fan 25 continues operation for a short period of time after cut-off of the main heater.

Figure 6:
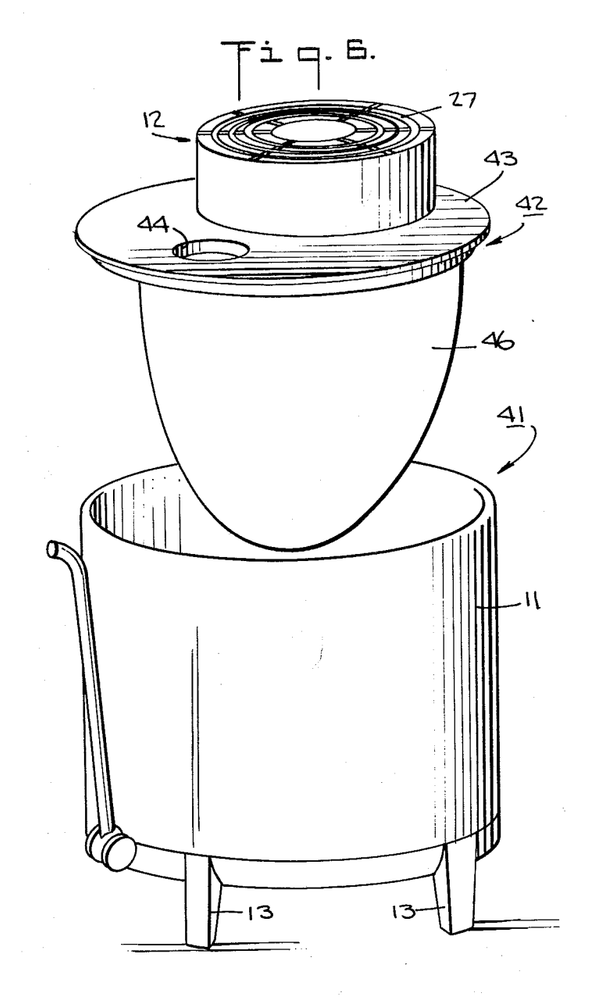
FIG. 6 illustrates an exploded view of a modified water distiller according to the invention utilizing a flexible impermeable partition.
Figure 7:
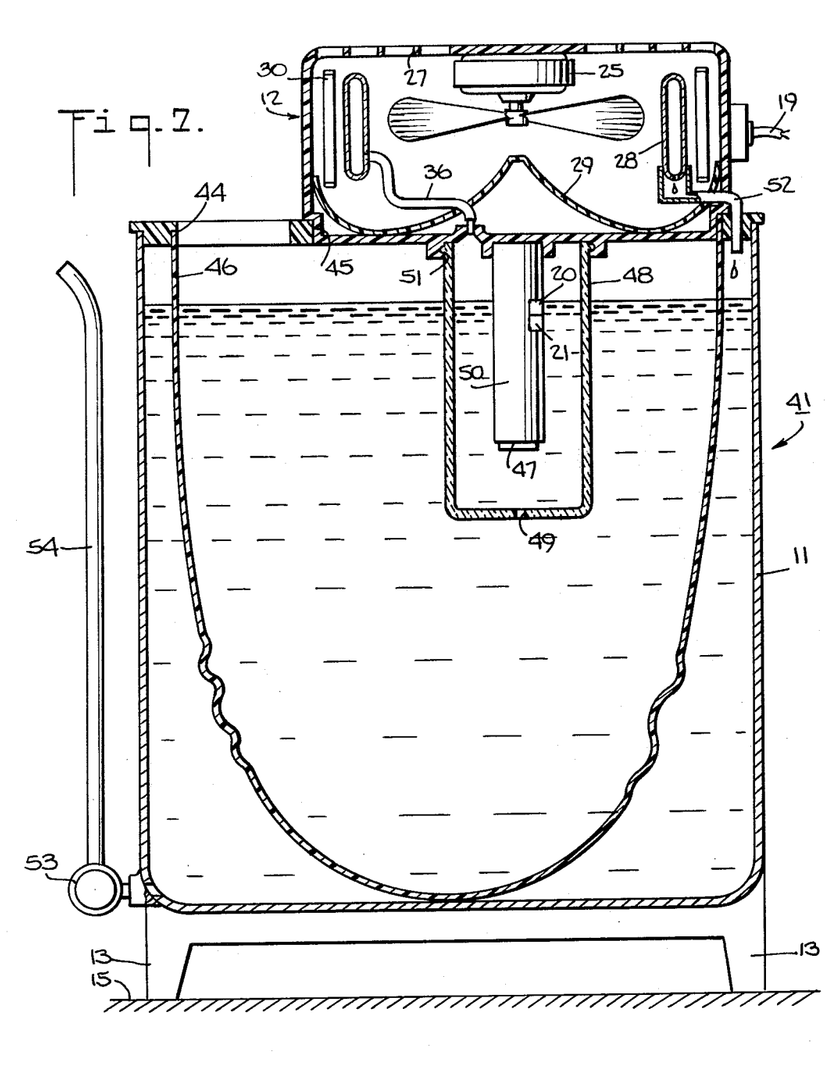
FIG. 7 illustrates a cross-sectional view of the water distiller of FIG. 6.

Referring to FIGS. 6 and 7, wherein like reference characters have been used to indicate like parts as above, the water distiller 41 may also be made to retain the distilled water therein. To this end, a cap assembly 42 is mounted on a housing 11. This cap assembly 42 includes a cover 43 which has an inlet 44 for introducing water into the housing 11 and a recess 45 into which a radiator-fan cap 12 fits. The cover 43 has a flexible impermeable partition in the form of a bag 46 secured to the cover 43 to depend into the housing 11. In addition, a heater 47 is mounted from the radiator-fan cap 12 in depending fashion. Also, a boiler 48 in the form of a tubular member 49 is secured to the base of the cap 12 about the heater 47 so as to form a confined space. This boiler 48 is provided with an inlet 49' to communicate the interior of the boiler 48 with the space within the bag 46. In this way, water is allowed to enter into the boiler 48 and achieve the same level as the water within the bag 43. As above, a flexible conduit 36 communicates the interior of the boiler 48 with the inlet to the radiator 28.

Referring to FIG. 7, the heater 47 is mounted on the cover by means of a depending tongue 50. In addition, the tongue 50 carries an auxiliary heater 21 and thermostat 20 for purposes similar to that described above. The boiler 48 is also secured to the cap 12 within a socket 51. To this end, the socket 51 and boiler 48 may be threaded to provide a threaded fit or the boiler 48 may be press-fit into the socket 51. In either case, the socket 51 is fixedly secured to the cap 12.

As shown in FIG. 7, an outlet tube or pipe 52 located under the radiator outlet communicates directly through the cover 43 into the interior of the housing 11 outside of the bag 46.

As also shown, a suitable spigot valve 53 is secured at a lower end of the housing 11 to communicate with the interior of the housing 11. A fold-down tube 54 is hingedly mounted on the spigot valve 53 to be selectively communicated with the interior of the housing 11. In use, when the tube 54 is moved into a horizontal position, the spigot valve 53 is opened so that distilled water within the housing 11 can be dispensed.

Both the fan 25 and the heater 47 are connected via suitable electrical lines 19 to a power source (not shown) so as to be operated individually from each other via suitable switches or in common via a single switch.

In operation, with the distiller turned on, raw water within the boiler 48 is heated by the main heater 47 and vaporizes. The vaporized water then passes to the conduit and into the radiator. After condensing, the water drips through the outlet tube 52 into the interior of the housing 11 outside of the bag 46.

Initially, when the distiller 41 is filled with water, the bag 46 occupies substantially all of the space within the housing 11. However, during distillation, the distilled water fills the space between the bag 46 and the housing 11. Because the bag is flexible the water level within this space remains the same as the water level within the bag 46. As a result, the bag 46 slowly collapses to a position about the boiler 48 as the volume of distilled water builds up. As also shown in FIG. 7, the water levels in the various spaces defined by the housing, bag and boiler are the same.

Should insufficient water remain within the housing 11, the water level within the boiler 48 drops below the auxiliary heater 21. This, in turn, causes a shut-down of the distiller in the manner described above.

As shown in FIG. 6, the cap assembly 42 can be mounted on the housing 11 as a unit. Of course, the construction of the distiller is such that the cover 43 may remain in place on the housing 11. Thus, the various components may be individually removed for example for cleaning purposes.

Referring to FIG. 7, the bag 46 may be secured to the cover in any suitable manner and may be permanently fixed in place or mounted so as to be replaced over a course of time.

Figure 8:
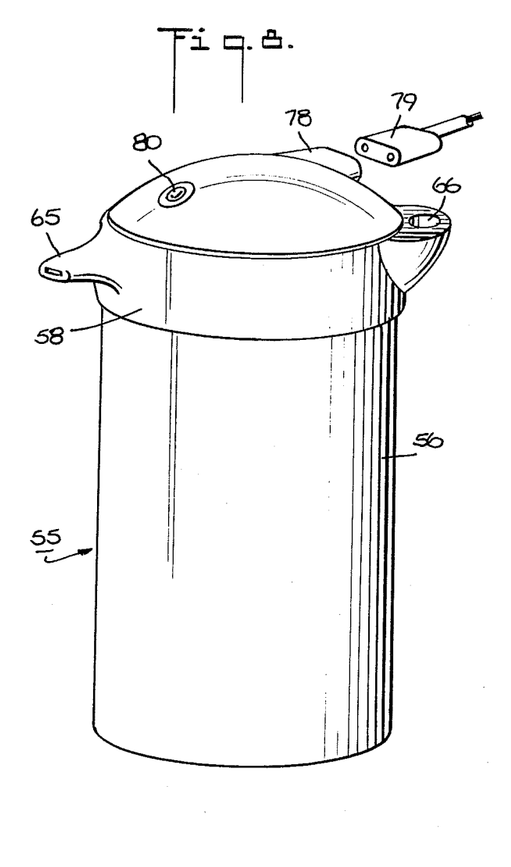
FIG. 8 illustrates a perspective view of a further modified water distiller according to the invention.
Figure 9:
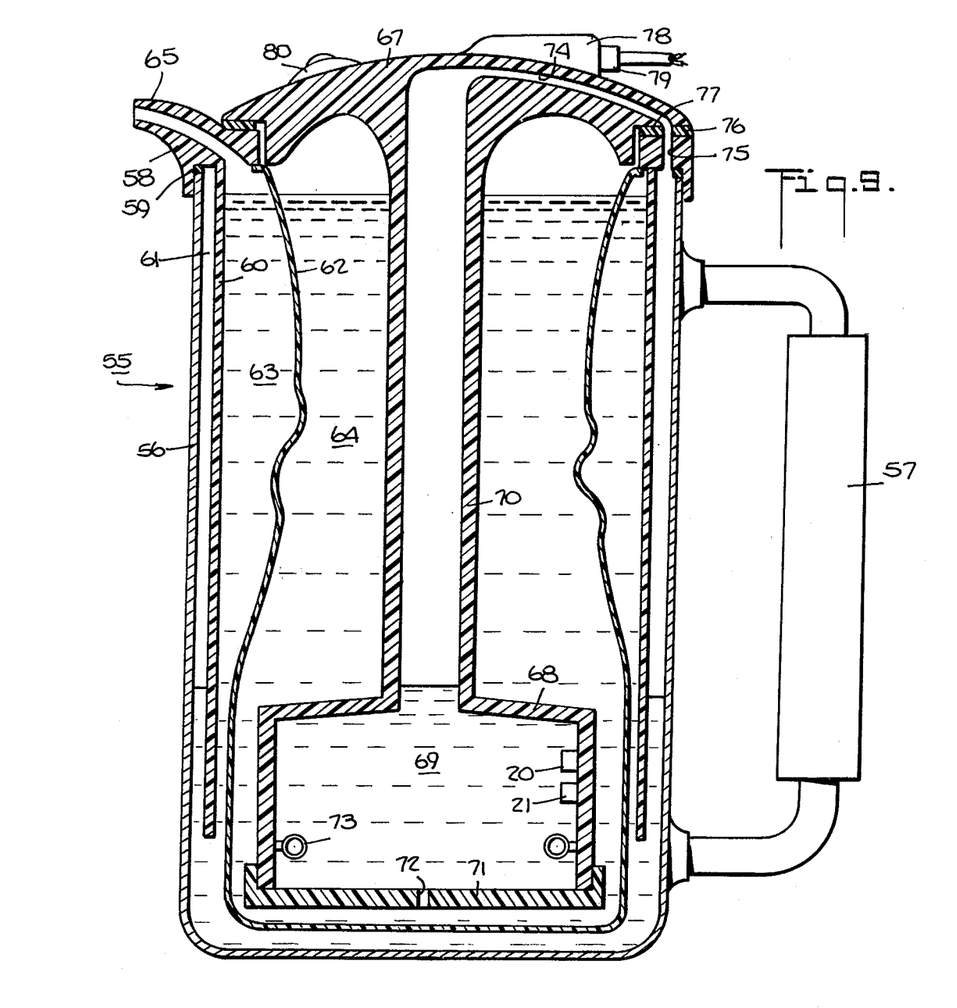
FIG. 9 illustrates a cross-sectional view of the distiller of FIG. 8.

Referring to FIGS. 8 and 9, the water distiller may be constructed without a radiator-fan cap. To this end, the distiller 55 has a housing 56 of cylindrical contour which is provided with a handle 57 so as to be lifted and manipulated.

A member 58 of annular shape is mounted as a collar on the housing 56 at the upper end in seal-tight relation. In addition, a gasket 59 is carried by the member 58 for sealing against the upper rim of the housing 56. The member 58 includes a tubular wall 60 which depends into the housing 56 in spaced concentric relation to the inner wall of the housing in order to define a space 61 therebetween. In addition, the member 58 carries a flexible and impermeable bag 62 which also depends into the housing within the tubular wall to define a space 63 between the bag 62 and the tubular wall 60 as well as a space 64 within the bag 62. The member 58 is also formed with a spout 65 which communicates with the space 63 between the tubular wall 60 and the bag 62.

As shown in FIG. 8, the member 58 also includes an inlet 66 which communicates with the space 64 within the bag 62 so that the bag 62 may be filled with water. In a similar fashion, the brine spout (not shown) with a cap is also formed in the member 58 which communicates with the interior of the boiler 68 so that spent water or brine may be poured off.

Referring to FIG. 9, a boiler cap assembly 67 is mounted on the annular member 58 and includes the boiler 68 which depends downwardly into the bag 62 to define an enclosed space 69. The boiler 68 is shown mounted on the lower end of a tube 70. The boiler 68 includes a substantially inverted cup-shaped member integral with the depending tube 70 and a removable cap 71 which is detachably connected by threading or press fitting on the lower end of the boiler 68. This cap 71 includes an inlet hole or port 72 which communicates the interior of the boiler 68 with the bag interior. In this way, water within the bag 62 is able to flow into the boiler space 69. A heater 73 is also mounted within the boiler in order to vaporize water within the boiler space 69. As above, the boiler 68 is also provided with a heater-thermostat shut-off means 20, 21.

The main heater 73 is constructed of any suitable shape, for example as shown in the form of a coil.

The boiler cap assembly 67 also includes a means which communicate the boiler space 69 with the space 61 between the tubular wall 60 and the housing 56 in order to deliver vapor thereto for condensing purposes. As shown, this means includes an internal duct 74 which communicates the depending tube 70 with the space 61 via an opening 75 in the member 58. This opening 75 may be oversized with respect to the duct 74 in order to allow some range of movement therebetween in order to communicate the duct 74 with the space 61. For example, the opening 75 may be an elongated slot as viewed from the top.

The boiler cap assembly 67 is mounted in seal-tight relation with the annular member 58 and to this end, a pair of annular gaskets 76, 77 as disposed therebetween. As shown in FIG. 7, these annular gaskets 76, 77 are disposed to either side of the duct 75.

A suitable electrical socket 78 is mounted within the boiler cap assembly 67 which is adapted to receive an electrical plug 79 for supplying power to the electric heater 73 and the heater-thermostat shut-off means 20, 21 within the boiler 68. In addition, an indicator light 80 is mounted on the top of the boiler cap assembly 67 to indicate when the distiller 55 has been shut-off by the thermostat 20. This light 80 is connected in parallel with thermostatic switch 20.

The boiler 68 is generally constructed of stainless steel which is double walled with glass wool insulation. The housing 56 is likewise made of stainless steel while the annular member 58 can be made of plastic.

The diameter of the tube 60 is slightly less than the inside of the housing 56 so as to leave a space of about ¼ inch between the tube and the housing. In addition, the tube extends downward to within an inch or so of the housing bottom.

In operation, water is poured into the inlet 66 to fill the bag 62. Thereafter, the power is turned on so that the heater 73 begins to vaporize the water which has entered into the boiler 68. Thereafter, bubbles of vapor are formed within the boiler 68 and pass upwardly through the tube 70. Next, the vapor passes through the duct 74 downwardly into the space 61 between the depending tube 60 and the housing 56. The heat of the vapor is conducted through the housing walls and dispersed by radiation and by convection cooling. To enhance radiation, the outside of the housing may be painted with a dark paint. In addition, the inner tubular wall 60 permits cooling of the vapor by a heat exchange relation with the water within the interior of the bag 62 and the space 63 between the bag 62 and the tube 60. The condensed vapor then falls to the bottom of the housing 56 and begins to fill the housing 56 to both sides of the wall 60. Continued operation results in the flexible bag 62 rumpling and contracting about the tube 70 and boiler 68 while the space between the bag 62 and housing 56 fills with distilled water. In normal operation, the heater wattage is chosen so that a pressure of about 5 to 7 inches of water is present in the boiler 68. As a result, the water level in the boiler 68 and the space 61 between the wall 60 and housing 56 is at about the top of the bulbous lower portion of the boiler 68, that is, about 5 to 7 inches below the level of the water in the distiller housing proper.

Eventually, the water within the bag 62 is exhausted and the water within the boiler 58 starts to drop. The unit then turns itself off, for example, about 24 hours after being turned on. The remaining brine may be removed by tilting the distiller 55 sideways and to the right after unscrewing the cap to the brine spout. This spout is connected by a tube (not shown) to the boiler tube 70.

In order to dispense the distilled water, the distiller is tilted forward so that the distilled water flows out of the spout 65.

Figure 10:
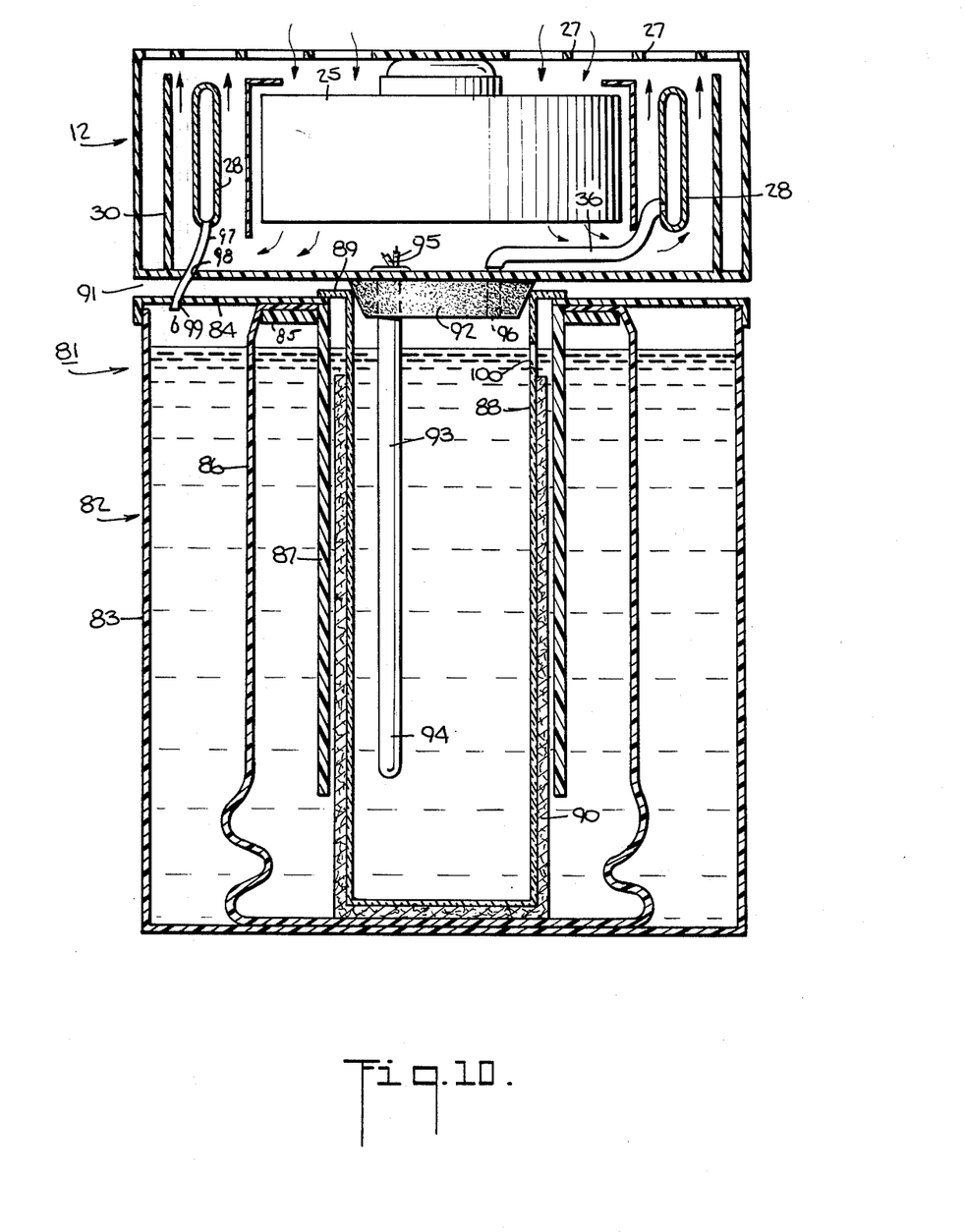
FIG. 10 illustrates a cross-sectional view of a further modified water distiller according to the invention.

Referring to FIG. 10, where like reference characters indicate like parts as above, the water distiller 81 is of generally a two component structure. One component 82 is formed of a housing 83 with a suitable base. The housing 83 is of generally cylindrical construction with an open top and is provided with a closure cap 84 which seats on the base 83. This cover 84 carries an annular ring 85, for example of plastic which fixedly secures a flexible water impermeable bag 86 thereto in depending fashion. For example, the bag 86 may be made of polyethylene. The ring 85 is secured to the cover 84 of the housing in any suitable fashion, for example by means of threaded bolts, rivets or screws. In addition, a Lucite tube 87 is mounted in fixed relation within the ring 85 for example in a press fit manner.

The housing 83 receives a boiler 88 which passes through an opening in the cover and telescopes into the Lucite tube 87 and which is of double walled glass construction and which has a lip 89 at the upper end so as to form an open mouth. As shown, the lip 89 extends over the cover 84 of the housing. The boiler 88 also includes glass wool 90 insulation between the glass walls. The boiler 88 is sized to entend downwardly into the housing 82 to seat on the bag 86 and the floor of the housing. The Lucite tube 87 serves to prevent sideways motion of the boiler 88 within the housing 83.

The second component of the distiller is formed of a radiator-fan assembly 12. This assembly is constructed in a similar fashion to that described above in FIG. 7. In addition, the radiator-fan cap 12 has a depending skirt which fits snugly about the outer wall of the housing 83. Also, a stopper 92 such as rubber is mounted on the bottom of the cap 12 in any suitable manner such as by means of adhesives or bolts. The stopper 92 is sized to sealingly engage in the open mouth of the boiler 88 and for this purpose is formed of any suitable material. The stopper also has an elongated rod 93 depending therefrom which passes into the boiler 88 to mount a heater 94 therein. This heater 94 is electrically connected via suitable leads 95 to a terminal within the cap 12. Also, the stopper 92 has a duct 96 passing therethrough which communicates via a suitable flexible conduit 36 or the like to the radiator 28.

Also, the outlet end of the radiator 28 is connected by a conduit or hose 97 through an opening 98 in the base of the cap 12 and an opening 99 in the cover 84 so as to dispense distilled water into the housing 83 in the space between the bag 86 and housing wall 83.

Referring to FIG. 10, the boiler 88 is provided with at least one small opening 100 above the insulation 90 so as to communicate the interior of the boiler with the bag interior.

In operation, the radiator-fan cap 12 is removed from the housing proper and water is introduced into the bag 86. This may be accomplished with the boiler 88 removed or with the boiler 88 in place. In the latter case, the water is introduced into the boiler 88 and when the water level reaches the opening 100, the water will then flow into the bag 86 until the bag 86 completely or substantially completely fills the housing 83. Thereafter, the radiator-fan cap 12 is placed down over the housing 83 with the stopper 92 sealingly closing the boiler 88. Thereafter, power is turned on and the heater 94 begins to vaporize the water within the boiler. The vapor then passes through the duct 96 in the stopper 92 and passes through the conduit 36 into the radiator 28. As above, the vapor within the radiator 28 is then condensed by the air flowing over the radiator 28 via the fan 25. The condensed vapor then passes out of the outlet end of the radiator 28 via the hose 98 into the housing space between the bag 86 and the housing wall 83. Continued operation causes the space outside of the bag 86 to fill with water so that the bag 86 collapses about the Lucite tube 87 and boiler 88.

The water distiller may also be provided with a suitable heat-thermostat shut-off means as above in order to shut-off the distiller when the level of water within the boiler falls below a certain level.

It is to be noted that the water level within the boiler 88, the bag 86 and the housing 83 is at the same level throughout operation.

The housing may be made of any suitable size, for example to contain 1 gallon of water. In addition, in order to provide for a lightweight construction, the housing may be made of a suitable plastic material such as polypropylene.

The heater may be of any suitable type such as a Vycor heater capable of producing 250 watts.

The radiator-fan assembly may also be provided with a suitable air baffle about the fan. Also, the air may flow directly downwardly on the floor or the cap so that the floor causes the air flow to move upwardly about both sides of the radiator which may be made of copper.

In any of the above embodiments, the bubble catcher tube or boiler is preferably a double walled aluminum or stainless steel tube with fiberglass insulation between the walls. However, a double walled plastic tube with foam plastic such as polyurethane insulation can be used or the boiler can be made of metal tubing such as aluminum or stainless steel without insulation.

Similarly, the radiator can be made with a single turn of a tube of copper which is tinned internally or of a suitable stainless steel. In one case, the radiator has a rectangular inside cross section of about two inches height and ¼ inch width. The tube is also bent into an almost complete circle on a radius of about five inches. Steam is caused to enter the tube at a level of about ½ inch to one inch above the bottom while water exits through an outlet hole which is open at the atmosphere and located at the bottom at the opposite end of the tube.

The inner surface of the radiator encircles the fan and acts as a Venturi for the fan. The blades of the fan have an outer diameter of about 4 inches and rotate in a horizontal plane so as to draw into the central portion of a grill and the surface of the fan-radiator cover. The fan is fastened to the grill and is of any standard commercial type, for example, The RuTron Co., "Muffin" fan consuming about 15 watts of power and blowing about 100 cubic feet of air per minute (free flow).

The radiator can also be constructed using a plastic such as Teflon provided the thickness of the plastic separating the air and vapor is, for example less than about 0.02 inches.

The invention thus provides a water distiller of compact construction. For example, the ratio of the volume of the distiller and the storage space to the volume of water distilled per cycle is in the order of 2½ for the embodiment in FIG. 1 and 1½ for those in FIGS. 7 and 9. In addition, the distiller provided by the invention consumes relatively low power, for example 3 killowatt hours for each gallon of water distilled. Also, the distiller can be manufactured at a relatively low cost due to the simplicity of the parts involved.

Because the optimum design of a water distiller producing 1 gallon per day is not the same as that of one capable of producing 2 or 3 gallons per day, various embodiments have been described above. In the case of the embodiment illustrated in FIGS. 1 to 5, such as capable is supplying a family of two to six persons, assuming a consumption of about ½ gallon per day per person. The embodiment illustrated in FIGS. 6 and 7 is a more compact unit for a family of three to six persons and the embodiment of FIGS. 8 and 9 may be used for a single person.

In the case of the embodiments illustrated in FIGS. 6, 7 and 10, the fan-radiator cap is of relatively lightweight construction, for example about two pounds with a diameter of about 6 inches and a height of about 3 inches. As such, the assembly does not radically increase the volume of a gallon container which is about 6 inches in diameter and 8 inches high. An important feature of this assembly is that the distilled water outlet is high above a counter surface so that the distilled water storage space and the distiller can rest on the same counter.

The thermal insulation on the bubble catcher means or boiler ensures that most of the heat from the heater is used to turn water into steam or vapor rather than just leaking away through the housing sides.

The flexible impermeable bag which is utilized in the various embodiments allows the same housing to be divided into a raw water space and a distilled water space. This saves space since the bag eliminates the need for a separate storage vessel for the distilled water.

What is claimed is:

1. A water distiller comprising
   a housing defining a raw water storage space;
   a heater disposed in said housing for vaporizing water in said space; and
   a cap removably mounted on said housing in sealed relation to said housing, said cap having a radiator therein in communication with said raw storage space to receive a flow of vapor therefrom, a fan for blowing air over said radiator to condense the vapor therein to water and an outlet connected to said radiator for dispensing the water therefrom.

2. A water distiller as set forth in claim 1 wherein said radiator is a closed tube of arcuate shape and said fan is concentrically mounted therein to blow a flow of air under and around said closed tube.

3. A water distiller as set forth in claim 2 which further comprises a bubble catcher means within said housing above said heater for guiding bubbles of vaporized water upwardly towards said cap and a conduit in said cap communicating said bubble catcher means with the interior of said closed tube at one end of said tube, said outlet being connected at an opposite end of said tube.

4. A water distiller as set forth in claim 3 wherein said bubble catcher means is a thermally insulated tube.

5. A water distiller as set forth in claim 3 further comprising a heater-thermostat shut-off means for deactivating said heater in response to the water level in said housing falling below a predetermined level.

6. A water distiller as set forth in claim 1 wherein said outlet communicates with the exterior of said housing.

7. A water distiller as set forth in claim 1 wherein said radiator includes at least one tubing turn disposed in an arcuate manner and said fan is mounted concentrically within said radiator, said radiator having an inside surface defining a venturi for said fan.

8. A water distiller as set forth in claim 7 which further comprises cooling fins on said radiator.

* * * * *